(12) United States Patent
Maxwell et al.

(10) Patent No.: US 10,130,451 B2
(45) Date of Patent: Nov. 20, 2018

(54) ULTRASONIC TIP ASSEMBLY

(71) Applicant: DENTSPLY SIRONA Inc., York, PA (US)

(72) Inventors: Randall Maxwell, Broken Arrow, OK (US); Kevin Wilkinson, Bixby, OK (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/785,621

(22) Filed: Oct. 17, 2017

(65) Prior Publication Data

US 2018/0036105 A1 Feb. 8, 2018

Related U.S. Application Data

(62) Division of application No. 14/162,793, filed on Jan. 24, 2014, now Pat. No. 9,820,834.

(60) Provisional application No. 61/756,253, filed on Jan. 24, 2013.

(51) Int. Cl.
*A61C 5/00* (2017.01)
*A61C 17/02* (2006.01)
*A61C 3/03* (2006.01)
*A61C 5/42* (2017.01)
*A61C 17/06* (2006.01)

(52) U.S. Cl.
CPC ............ *A61C 17/0202* (2013.01); *A61C 3/03* (2013.01); *A61C 5/42* (2017.02); *A61C 17/02* (2013.01); *A61C 17/0208* (2013.01); *A61C 17/043* (2013.01)

(58) Field of Classification Search
CPC .. A61C 5/02; A61C 5/42; A61C 17/02; A61C 17/0208; A61C 17/0202; A61C 17/043; A61C 3/03; A61C 19/041
See application file for complete search history.

(56) References Cited

U.S. PATENT DOCUMENTS

| 4,608,017 | A | * | 8/1986 | Sadohara | A61C 5/40 433/81 |
| 6,464,498 | B1 | * | 10/2002 | Pond | A61C 17/0202 433/81 |
| 6,494,713 | B1 | * | 12/2002 | Pond | A61C 5/40 433/224 |
| 2009/0111068 | A1 | * | 4/2009 | Martinez | A61C 17/0208 433/81 |

(Continued)

*Primary Examiner* — Glenn Richman
(74) *Attorney, Agent, or Firm* — Dentsply Sirona Inc.

(57) ABSTRACT

A tip assembly for use with a dental tool, the tip assembly comprising a housing for attaching to the dental tool, at least one aspiration needle having a passageway extending at least partially through the aspiration needle, a substantial length of the aspiration needle, or at least from one end to the other end of the aspiration needle, the passageway providing a single continuous path to aspirate the irrigant and/or debris from the root canal cavity of the tooth, and at least one irrigation needle having a passageway extending at least partially through the irrigation needle, a substantial length of the irrigation needle, or at least from one end to the other end of the irrigation needle, the passageway provides a continuous flow path for delivering fluid/irrigant from a reservoir in communication with a proximal end of the irrigation needle to the distal end of the irrigation needle and into a root canal/coronal opening of a tooth.

7 Claims, 13 Drawing Sheets

(56) References Cited

U.S. PATENT DOCUMENTS

2010/0190133 A1* 7/2010 Martinez ............ A61C 17/0208
433/81

* cited by examiner

SECTION B-B

SECTION C-C

DETAIL D

SECTION A-A

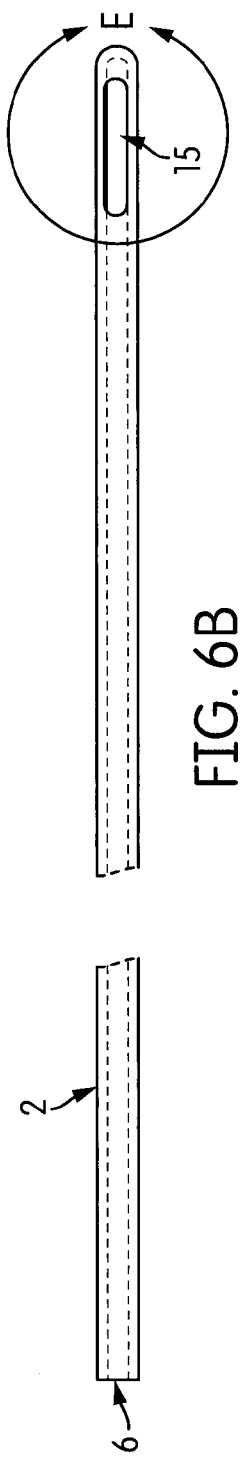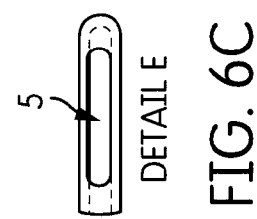
FIG. 6A
FIG. 6B
FIG. 6C

DETAIL A

ULTRASONIC TIP ASSEMBLY

CROSS-REFERENCE TO RELATED APPLICATIONS

This is a Divisional Application of Ser. No. 14/162,793, filed on Jan. 24, 2014, which of claims the benefit of and priority to U.S. Provisional Patent Application Ser. No. 61/756,253, filed on Jan. 24, 2013, which are herein incorporated by reference for all purposes.

FIELD OF THE INVENTION

The present invention is directed to a device for performing dental procedures, and specifically to an ultrasonic tip assembly, useful for delivering and agitating irrigants as well as aspirating said irrigants in root canal therapy, i.e. endodontics.

BACKGROUND OF THE INVENTION

This invention relates to dental instruments and particularly to endodontic instruments, systems and procedures for treating a tooth root canal in which the root canal is cleansed of bacteriological materials by physical and acoustic debridement and flushing with an irrigation solution, particularly the apparatus and equipment for providing irrigation to remove diseased and necrotic tissue, and providing aspiration to remove the irrigation solution and resulting debris.

Endodontics has become an important part of dentistry. Prior to common use of endodontic procedures, an abscessed tooth was typically treated only by extraction of the tooth. However, since the advancement of endodontics, abscessed teeth can be successfully treated to permit retention by a patient, for greatly increased health and physiological benefit. Endodontics has been one of the great advances in modern medicine.

The endodontic preparation of a root canal typically includes opening the root canal through the coronal area of the tooth and thereafter manipulating files and reamers within the root canal to physically remove as much as possible of the pulpal material. The pulpal material is typically infected or necrotic, that is, dead material; and any such material that remains in the root canal after the procedure is completed is a source of potential infection. For this reason, proper treatment of a root canal attempts to remove as much of the necrotic pulpal material as is possible. By use of files and reamers, a substantial portion of such pulpal material can be removed; however, it is virtually impossible in most cases to remove all such material by physical manipulation of tools within the canal. For this reason, in recent times procedures have been developed wherein the root canal is irrigated or flushed with a fluid to remove and/or neutralize organic pulpal material that remains after files and reamers have been employed and then the pulpal material and fluid is removed through aspiration.

Previous ultrasonic tips, including prior art (Maxwell US 2011/0020765 A1), which is herein incorporated by reference, were powered by an L-mode (longitudinal mode) transducer system, which results in vibrations of the tip of the needle in a 2-dimensional direction longitudinally; the resulting vibrations are in a single plane. The present invention is optimized to result in 3-dimensional vibrations being multi-planar, which may be accomplished while being utilized with an L-T (longitudinal-torsional) mode transducer system (see Bromfield, US Patent US App 2009/0236938 A1), which is herein incorporated by reference. The resulting vibration pattern resembles a multi-noded "jump rope" or whipping vibration around the long axis. The benefits of L-T mode transducer systems provide for better agitation of irrigant and acoustic debridement inside the root canal over just an L-mode transducer. It is believed that the resulting vibration pattern from use with an L-T mode transducer system may also be safer for the patient over prior art in that the motion will be circular and distribute the heat around the circumference of the canal and not be locally isolated inside the canal. The circular motion should also tend not to enlarge the existing root canal.

Another problem associated with the prior ultrasonic tips is the limited insertion depth into the root canal due to bulky apparatuses and/or material thicknesses to achieve designs resulting in the necessary resonance to clean the respective root canal. The present invention allows for use of smaller gauge needles as compared to prior art which in turn allows for the inner aspirating needle to reach deeper into the root canal for better cleaning closer to the apex.

SUMMARY OF THE INVENTION

The present invention is directed to a device for performing dental procedures, and specifically to an ultrasonic tip assembly, that may be optionally driven by an L-T mode transducer system, useful for delivering and agitating irrigants as well as aspirating said irrigants in root canal therapy, i.e. endodontics.

Aspects of the present invention seek to improve upon prior art by providing for an ultrasonic tip having a geometry that may include an aspirating needle extending beyond and being surrounded by at least one and preferably a plurality of outer irrigating needles.

In another aspect, the present invention contemplates a tip assembly for use with a dental tool, the tip assembly comprising: a housing for attaching to the dental tool; at least one aspiration needle having a passageway extending at least partially through the aspiration needle, a substantial length of the aspiration needle, or at least from one end to the other end of the aspiration needle, the passageway providing a single continuous path to aspirate the irrigant and/or debris from the root canal cavity of the tooth; at least one irrigation needle having a passageway extending at least partially through the irrigation needle, a substantial length of the irrigation needle, or at least from one end to the other end of the irrigation needle, the passageway provides a continuous flow path for delivering fluid/irrigant from a reservoir in communication with a proximal end of the irrigation needle to the distal end of the irrigation needle and into a root canal/coronal opening of a tooth; and wherein the aspiration needle and irrigation needle are connected together at a point or along a portion therebetween to achieve a first predetermined resonant frequency of the aspiration needle.

In another aspect, the present invention contemplates a tip assembly for use with a dental tool, the tip assembly comprising: a housing for attaching to the dental tool, the housing having a receiving portion; an inner aspiration needle having a passageway extending at least partially through needle, substantial length of the needle, or at least from one end to the other end the passageway providing a single continuous path to aspirate the irrigant and debris from the root canal cavity of the tooth; a plurality of outer irrigation needles, surrounding inner aspiration needle, each having a passageway extending at least partially through the plurality of needles, substantial length of the plurality of needles, or at least from one end to the other end, the passageway provides a continuous flow path for delivering fluid/irrigant from a reservoir at the proximal end of the plurality of needles to a root canal/coronal opening of a tooth at the distal end of the plurality of needles; and wherein the inner aspiration needle and outer irrigation needles are connected together at a point or along a portion therebetween to achieve a first predetermined resonant frequency of the inner aspiration needle.

In another aspect, the present invention contemplates a tip assembly for use with a dental tool, the tip assembly comprising: a housing for attaching to the dental tool, the housing having a receiving portion; an inner irrigation needle having a passageway extending at least partially through needle, substantial length of the needle, or at least from one end to the other end, the passageway providing a single continuous flow path for delivering fluid/irrigant from a reservoir at the proximal end of the irrigation needle to a root canal/coronal opening of a tooth at the distal end of the irrigation needle; a plurality of outer aspiration needles, surrounding inner irrigation needle, each having a passageway extending at least partially through the plurality of aspiration needles, substantial length of the plurality of aspiration needles, or at least from one end to the other end, the passageway providing a single continuous path to aspirate the irrigant and debris from the root canal cavity of the tooth; wherein the inner irrigation needle and the plurality of outer aspiration needles are connected together at a point or along a portion therebetween to achieve a first predetermined resonant frequency of the outer aspiration needles.

In another aspect, the present invention contemplates a tip assembly for use with a dental tool, the tip assembly comprising: a housing having a conduit for attaching to the dental tool; an inner aspiration needle having a passageway extending at least partially through needle, a substantial length of the needle, or at least from one end to the other end the passageway providing a single continuous path to aspirate the irrigant and debris from the root canal cavity of the tooth; a plurality of outer wires, surrounding inner aspiration needle; and wherein the inner aspiration needle and outer wires are connected together at a point or along a portion therebetween to achieve a first predetermined resonant frequency of the inner aspiration needle.

In another aspect, the present invention contemplates a tip assembly for use with a dental tool. The tip assembly has an insert, an inner aspiration needle, a plurality of outer irrigation needles and a housing. The insert attaches to the dental tool and has a conduit. The inner aspiration needle has a passageway extending at least partially through the needle, substantial length of the needle or at least from one end to the other end. The passageway provides for a single continuous flow path to aspirate the irrigant and debris from the canal cavity of the tooth. The plurality of outer irrigation needles each have a passageway extending at least partially through the needle, substantial length of the needle or at least from one end to the other end. The passageway provides a continuous flow path for delivering fluid/irrigant from a reservoir at the proximal end of the needle to a root canal of a tooth at the distal end of the needle. The housing covers at least a portion of the aspiration needle and irrigation needles. The aspiration needle and plurality of irrigation needles are brazed together at some point or points inside the housing.

In another aspect, the present invention contemplates a tip assembly for use with a dental tool. The dental tool may include an L-T mode ultrasonic energy generator positioned therein. The tip has an insert, an inner aspiration needle, a plurality of outer irrigation needles and a housing. The insert attaches to the dental tool and has a receiving portion. The inner aspiration needle has a passageway extending therethrough from a proximal end of the needle to a distal end of the needle. The passageway provides for a single continuous flow path to aspirate the irrigant and debris from the canal cavity of the tooth. The plurality of outer irrigation needles each have a passageway extending therethrough from a proximal end of the needle to a distal end of the needle. The passageway provides a continuous flow path for delivering fluid/irrigant from a reservoir at the proximal end of the needle to a root canal of a tooth at the distal end of the needle. The housing is molded over at least a portion of the aspiration needle and irrigation needles. The aspiration needle and plurality of irrigation needles are brazed together inside the housing. Energy generated by the ultrasonic energy generator driven by a L-T mode transducer is translated into movement of the single aspiration needle, as well as movement of the plurality of irrigation needles; the movement of the aspiration needle being multi-planar to the longitudinal axis of the needle to provide optimum cleaning of the root canal.

In another aspect, the present invention contemplates a tip assembly for use with a dental tool. The dental tool has an energy generator positioned therein. Although this energy generator is usually an L-T mode ultrasonic energy generator, other energy generators may be used, such as for example an L-mode ultrasonic energy generator. The tip assembly has an insert, an inner aspiration needle, a plurality of outer irrigation needles and a housing. The insert attaches to the dental tool and has a receiving portion. The inner aspiration needle has a passageway extending therethrough from a proximal end of the needle to a distal end of the needle. The passageway provides for a single continuous flow path to aspirate the irrigant and debris from the canal cavity of the tooth. The plurality of outer irrigation needles each have a passageway extending therethrough from a proximal end of the needle to a distal end of the needle. The passageway provides a continuous flow path for delivering fluid/irrigant from a reservoir at the proximal end of the needle to a root canal of a tooth at the distal end of the needle. The housing covers at least a portion of the aspiration needle and irrigation needles. The aspiration needle and plurality of irrigation needles are brazed together inside the housing. The insert cooperates with the needle to transfer energy from the energy generator through the insert to the needle. The fluid has the energy imposed thereon as it passes through the needle.

In yet another aspect, any of the aspects of the present invention may be further characterized by one or any combination of the following features: wherein the dental tool has an L-T mode ultrasonic energy generator positioned therein; wherein the energy generated by the ultrasonic energy generator is translated into movement of the aspiration needle to provide optimum cleaning of the root canal; wherein the energy generated by the ultrasonic energy generator is translated into movement of the irrigation needle inside the coronal aspect of the tooth to provide optimum cleaning of the root canal and/or pulp chamber; wherein the at least one irrigation needle is a plurality of irrigation needles is between 2-5; wherein the at least one aspiration needle is a plurality of aspiration needles is between 2-5; wherein the at least one irrigation needle is connected to the at least one aspiration needle at a point or along a portion therebetween inside the housing; wherein the at least one irrigation needle dampen vibrations and allow the at least one aspiration needle to vibrate on its own at the first predetermined resonant frequency; wherein the at least one irrigation needle vibrates at a second predetermined resonant frequency inside the coronal opening of a tooth, the first predetermined resonant frequency of the at least one aspiration needle being different than the second predetermined resonant frequency of the at least one irrigation needle; wherein the at least one aspiration needle and/or the at least one irrigation needle is straight, bent, or curved; wherein the at least one aspiration needle and the at least one irrigation needle are straight; wherein at a tip portion of the at least one irrigation needle is bent or curved away from the at least one aspiration needle; wherein at a tip portion of the at least one aspiration needle is bent or curved away from the at least one irrigation needle; wherein the at least one irrigation needle extends spirally around the at least one aspiration needle; wherein the at least one irrigation needle includes a first irrigation needle and a second irrigation needle, the first irrigation needle extending spirally around the at least one aspiration needle and a tip portion of the second irrigation needle being bent or curved away from the at least one aspiration needle; wherein the at least one aspiration needle extends spirally around the at least one irrigation needle; wherein the at least one aspiration needle includes a first aspiration needle and a second aspiration needle, the first aspiration needle extending spirally around the at least one irrigation needle and a tip portion of the second aspiration needle being bent or curved away from the at least one irrigation needle; wherein the at least one irrigation needle is shorter than the at least one aspiration needle; wherein the at least one aspiration needle and the at least one irrigation needle include a working portion such that a ratio of the working portion of the at least one aspiration needle to the working portion of the at least one irrigation needle ranges from about 0.5 to about 5, preferably from about 2 to about 4, and most preferably from about 2.5 to about 3.5; wherein the at least one aspiration needle is shorter than the at least one irrigation needle; wherein the at least one irrigation needle and the at least one aspiration needle include a working portion such that a ratio of the working portion of the at least one irrigation needle to the working portion of the at least one aspiration needle ranges from about 0.5 to about 5, preferably from about 2 to about 4, and most preferably from about 2.5 to about 3.5; wherein the at least one irrigation needle includes a plurality of irrigation needles having a working portion, the working portions varying in length; wherein the at least one aspiration needle includes a plurality of aspiration needles having a working portion, the working portions varying in length; wherein the plurality of irrigation needles have a working portion, the working portions having the same lengths or of varying lengths relative to each other so that they reach different depths of the coronal opening; wherein the plurality of aspiration needles have a working portion, the working portions having the same lengths or of varying lengths relative to each other so that they reach different depths of the coronal opening; wherein the at least one aspiration needle includes an inner aspiration needle and the at least one irrigation needle is a plurality of outer irrigation needles surrounding the inner aspiration needle; wherein the at least one irrigation needle includes an inner irrigation needle and the at least one aspiration needle is a plurality of outer aspiration needles surrounding the inner irrigation needle; wherein the at least one irrigation needle is only one irrigation needle and the at least one aspiration needle is only one aspiration needle juxtaposed to the only one irrigation needle; wherein the at least one aspiration needle and/or the at least one irrigation needle includes a working portion having a length that ranges from about 5 to about 40 mm; wherein the at least one aspiration needle and/or the at least one irrigation needle includes a working portion having a length that ranges from about 15 to about 30 mm; wherein the at least one aspiration needle and/or the at least one irrigation needle includes a working portion having a length that ranges from about 2 to about 10 mm; wherein the at least one aspiration needle and/or the at least one irrigation needle includes a working portion and a proximal portion such that a ratio of the working portion to the proximal portion 18 ranges from about 0.25 to about 3.0, and preferably from about 0.5 to about 2.5 (e.g., from about 1 to about 2); wherein the irrigation needles are the same lengths or of varying lengths relative to each other so that they reach different depths of the coronal opening; wherein the aspiration needles can be of the same lengths or of varying lengths relative to each other so that they reach different depths of the coronal opening; wherein the outer aspiration needles are shorter than the inner irrigation needle; wherein the outer aspiration needless are longer than the inner irrigation needle; wherein at a tip portion of the plurality of outer wires are bent or curved away from the aspiration needle; wherein the plurality of outer wires extend spirally around the aspiration needle; wherein the plurality of outer wires includes a first outer wire and a second outer wire, the first outer wire extending spirally around the aspiration needle and a tip portion of the second outer wire being bent or curved away from the aspiration needle; wherein the plurality of outer wires are solid; wherein the plurality of outer wires include a tip having a cutting edge; wherein the plurality of outer wires and the aspiration needle extend through an opening of the housing such that spacing is provided therebetween to allow fluid/irrigant to flow from the housing to a coronal opening of the root canal; or any combination thereof.

The invention described herein has many advantages. The needles have a single continuous flow path which eliminates potential leak paths. As no joints or discontinuities are present, corrosion is limited. Inherent stress concentrations are also eliminated, thereby allowing the tip assembly to be reliable during vibration. The configuration of the tip assembly guides and transfers the ultrasonic vibration and energy in the planes of motion, which provides proper agitation to the irrigants. The tip assembly is also disposable, thereby requiring that a new tip assembly may be used for each patient and insuring that the tip assembly will be sterile prior to use.

In a further embodiment of the invention, an abrading needle has an external groove or grooves that direct a flow of pressurized liquid toward a tip of the abrading needle. A sleeve may be positioned to surround the groove or grooves, thereby forming a flow channel there between.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings, which illustrate, by way of example, the principles of the invention.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIGS. 6A-6C illustrates various views of the inner aspiration needle of the tip assembly.

Figure 1A:
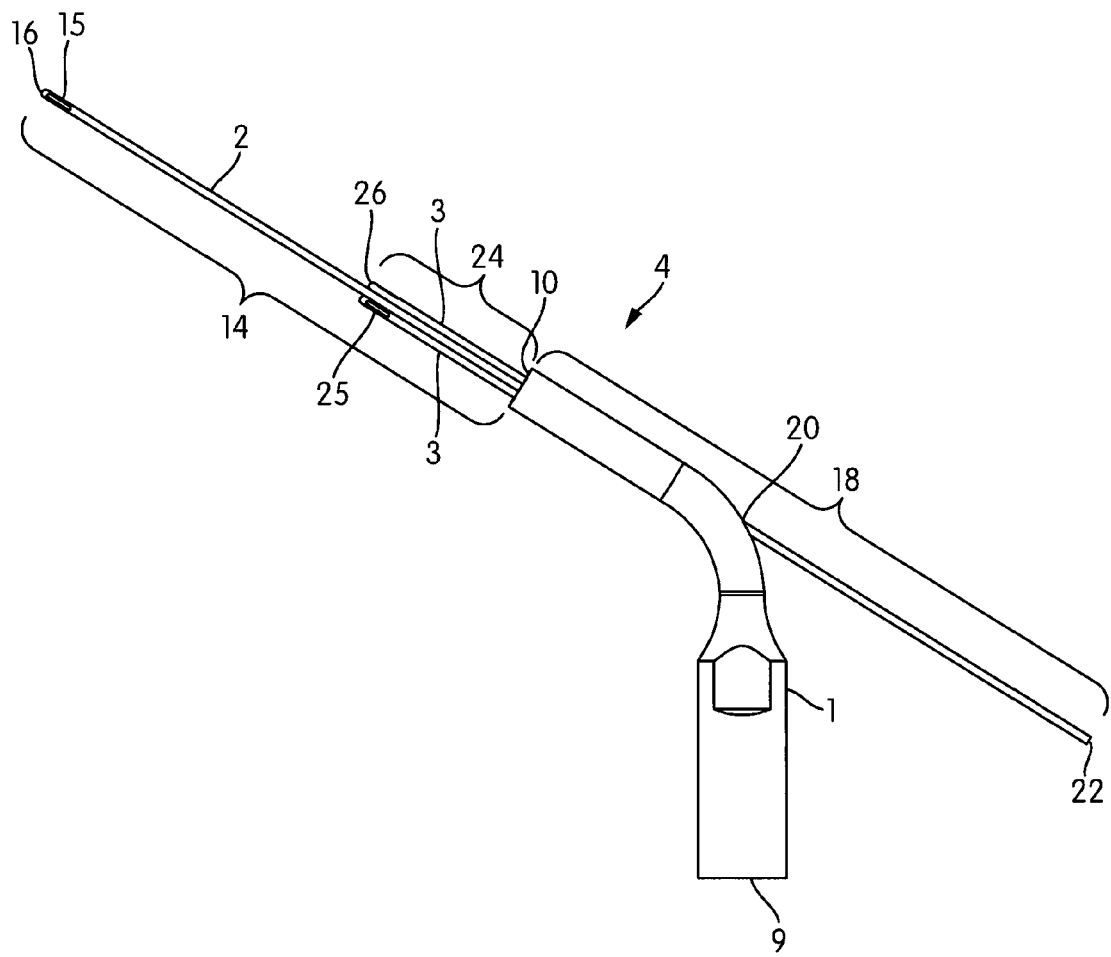
FIGS. 1A and 1B are diagrams illustrating perspective views of the ultrasonic tip assembly in accordance with embodiments of the present invention.
Figure 1B:
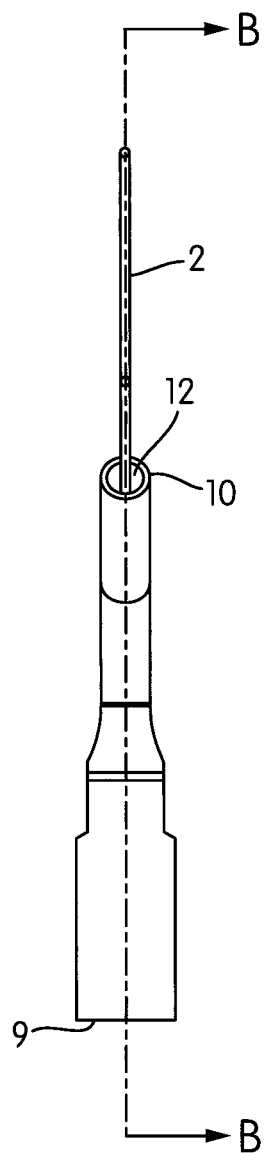

In the following description of the illustrated embodiments, references are made to the accompanying drawings, which form a part hereof, and in which is shown by way of illustration various embodiments in which the invention may be practiced. It is to be understood that other embodiments may be utilized and structural and functional changes may be made without departing from the scope of the present invention.

DETAILED DESCRIPTION OF THE INVENTION

The present invention is directed to a device for performing dental procedures, and specifically to an ultrasonic tip, and useful for delivering and agitating irrigants as well as aspirating said irrigants in root canal therapy, i.e. endodontics.

Generally, the present invention provides for an ultrasonic tip assembly comprising a housing for attaching to the dental tool (not shown). The housing includes a conduit (e.g., receiving portion or insert) for attachment to the dental tool and bore (e.g., central bore) for at least partially encasing as least one aspiration needle and at least one irrigation needle. The aspiration needle and/or the irrigation needle having a passageway extending at least partially through the needle, a substantial length of the needle, or at least from one end to the other end of the needle. The aspiration passageway provides a single continuous path to aspirate the irrigant and/or debris from the coronal opening and/or root canal cavity of the tooth. The irrigation needle passageway provides a continuous flow path for delivering fluid/irrigant from a proximal end of the irrigation needle (that may be in communication with a reservoir containing fluid/irrigant) to the distal end of the irrigation needle and into a root canal/coronal opening of a tooth. Desirably, the aspiration needle and irrigation needle are connected together at a point or along a portion therebetween to achieve a first predetermined resonant frequency (e.g., of the aspiration needle)

It is appreciated that the dental device (for use with the tip assembly) may include a wand that is a graspable and manipulatable hand piece. The wand of the dental device has a proximal end in communication with a housing of the tip assembly. Typically, the housing may be configured to engage the wand for removable securement thereto. In one specific example, the housing may include a receiving portion (e.g., a hollow bore) for receiving and engaging a portion of the wand, however, it is appreciated that the housing may be an insert that may be received by the wand. It is appreciated that the housing may be removably secured to the wand by known attachment means such as threaded cooperation, friction fit, welding, adhesive, and/or otherwise.

In a preferred embodiment, the wand includes an ultrasonic energy generator or transducer positioned in the wand proximate the proximal end. Desirably when included, the ultrasonic energy generator or transducer is an L-T mode (longitudinal-torsional) transducer system, though not required. However, L-mode (longitudinal mode) transducer systems, the like and/or otherwise are also contemplated as acceptable ultrasonic energy generators or transducers utilized in the dental device.

In one embodiment, the tip assembly may include at least one and preferably a plurality of (e.g., from 2 to 10 or from 2 to 5) irrigation needles positioned to concentrate vibrations resulting from the hand piece motor (e.g., ultrasonic energy generator, transducer, or otherwise) to at least one (e.g., from 1 to 5) aspiration needle. Although, the drawings generally depict an embodiment where the outer irrigation needles surround and inner aspiration needle, it is contemplated that the tip assembly may include one or more outer aspiration needles surrounded by one or more inner irrigation needles. In doing so, it is appreciated that the function of aspiration or irrigation may be independent of needle location relative to one another and therefore interchangeable with reference to either the outer needle or the inner needle being an aspiration needle or an irrigation needle.

When included, this orientation of outer irrigation needles relative to the inner aspiration needle allows for the inner aspiration needle to vibrate at (predetermined) resonant frequency It is believed that this resonant frequency in an L-T-mode ultrasonic handpiece may provide improved cavitation action and/or improved agitation of the irrigants inside the root canal as compared to an L-mode ultrasonic handpiece of the same or similar resonant frequency. Advantageously, the design of the present invention also provides for use of a smaller gauge needles to be used, which allows for the aspiration needle (or irrigation needle) to reach deeper into the root canal. While the inner aspiration needle may be focused into the root canal, the outer irrigation needle(s) are able to vibrate on their own at a (predetermined) resonant frequency (e.g., a different frequency than the resonant frequency of the aspiration needle) inside the coronal aspect of the tooth, the pulp chamber.

More particularly, a ultrasonic tip assembly 4 for use with a dental hand piece (optionally powered by an L-T mode transducer system, such as that described in US 2009/0236938 A1 by Bromfield, which is herein incorporated by reference for all purposes), includes a housing (e.g., brush holder) 1 for connecting to a dental handpiece, the housing encloses or encases at least a portion of the inner aspiration needle 2 and/or the outer irrigation needles 3. The outer irrigation needle(s) 3 may be secured to the inner needle 2 at a point or along a portion therebetween by any securement means known in the field (e.g., brazing welding, adhesive, or otherwise) to provide a generally liquid tight seal therebetween.

The aspiration and/or the irrigation needle may include a passageway extending at least partially therethrough (e.g., preferably a substantial length therethrough), or at least from one end to the other end of the passageway to providing at least one continuous path (for transporting a fluid such as a liquid, a gas, or otherwise, and combination thereof).

The aspiration and/or irrigation needles may be formed of any metals or alloys such as Stainless Steel, SMA material (e.g., Nitinol), Titanium, or otherwise). It is contemplated that the aspiration needle may be formed of the same material as the irrigation needle or a different material. Furthermore, the irrigation needles may be formed of the same material or different materials between the various included needles. The gauge of the material used for forming the aspiration and irrigation needles may be the same or different. Examples of needle gauge may range from about 25 gauge to about 30 gauge, and preferably from about 26 gauge to about 28 gauge). Desirably, the present invention provides for needles having a smaller gauge relative to prior art needles. This smaller gauge needle allows the tip to reach deeper into the apex of the tooth canal, thereby allowing for better debridement and cleaning of the root canal. It is appreciated that the aspiration and irrigation needles may be formed of same material with a similar gauge, though not required.

The housing 1 includes a distal free end 10 from which the inner aspiration needle 2 and the outer irrigation needles 3 extend outward of the housing for insertion into the root canal. The distal free end 10 may include one or more openings 12, respectively for receiving therethrough each of the aspiration and/or irrigation needles. As shown in one specific example (FIGS. 2B and 3), the distal free end includes a central opening 12a for receiving the inner aspiration needle therethrough and a plurality of outer openings 12b for receiving the outer irrigation needles therethrough. Optionally, the housing 1 may include at least one secondary opening 20 for receiving a second portion of the aspiration needle or irrigation needle therethrough.

The housing 1 may further include a conduit 9 for mating attachment the dental device (e.g., wand). It is appreciated that the housing 1 may be made from brass, aluminum, low carbon steel, or other metals and/or alloys, which have the strength and stability characteristics to mount the ultrasonic wand and withstand the vibration applied thereto. In one preferred embodiment, the holder 1 may be made from 17-4 Stainless Steel.

The aspiration needle 2 may include a working portion 14 that extends outward from the distal free end 10 of the housing 1 to a tip 16. It is appreciated that the working portion 14 of the aspiration needle 2 may extend from the distal free end 10 of the housing to the tip 16 at a length that ranges from about 5 to about 40 mm, and preferably from about 15 to about 30 mm. The working portion 14 may include at least one vented opening 5 for receiving the aspirated irrigants. The vented opening 5 may be located at the tip 16, proximal to the tip 16, or along any portion of the working portion 14. It is appreciated that when a plurality of vented openings 5 are included, various locations along the working portion 14 are contemplated such that the two or more of the openings 5 may be positioned radially from one another, longitudinally, or otherwise and combinations thereof. Furthermore it is appreciated that the vented opening 5 may be present in various sizes and or shapes (e.g., oval, circular, and/or otherwise). It is appreciated that the vented opening 5 may include a longitudinal length that ranges from about 0.5 to about 5 mm, and preferably from about 0.5 to about 2 mm. The aspiration needle 2 may further include proximal portion 18, which extends through the housing 1 from the opening 12 of the distal free end 10 and through a secondary (e.g., rearward) opening 20 and to a distal free end 22 of the aspiration needle. It is appreciated that a ratio of the working portion 14 of the aspiration needle 2 to the proximal portion 18 of the aspiration needle 2 may range from about 0.25 to about 3.0, and preferably from about 1 to about 2.

The irrigation needle 3 may include a working portion 24 that extends outward from the distal free end 10 of the housing 1 to a tip 26. It is appreciated that the working portion 24 of the irrigation needle 3 may extend from the distal free end 10 to the tip 26 at a length that ranges from about 1 to 15 mm, and preferably from about 2 to about 10 mm. The working portion 24 may include at least one vented opening 25 for delivering irrigant. The vented opening 25 may be located at the tip 26, proximal to the tip 26, or along any portion of the working portion 24. It is appreciated that when a plurality of vented openings 25 are included, various locations along the working portion 24 are contemplated such that the two or more of the openings 25 may be positioned radially from one another, longitudinally, or otherwise and combinations thereof. Furthermore it is appreciated that the vented opening 25 may be present in various sizes and or shapes (e.g., oval, circular, and/or otherwise). It is appreciated that the vented opening 25 may include a longitudinal length that ranges from about 0.5 to about 5 mm, and preferably from about 0.5 to about 2 mm. The irrigation needle 3 may further include proximal portion 28, which extends within the housing 1 from the opening 12 of the distal free end 10 to a distal free end 32. It is appreciated that a ratio of the working portion 24 of the irrigation needle 3 to the proximal portion 28 of the irrigation needle 3 may range from about 0.25 to about 3, preferably from about 0.5 to about 2.

Desirably, a ratio of the working portion of the aspiration needle to the working portion of the irrigation needle may range from about 0.5 to about 5, preferably from about 2 to about 4, and most preferably from about 2.5 to about 3.5; or a ratio of the working portion of the irrigation needle to the working portion of the aspiration needle may range from about 0.5 to about 5, preferably from about 2 to about 4, and most preferably from about 2.5 to about 3.5.

Figure 2A:
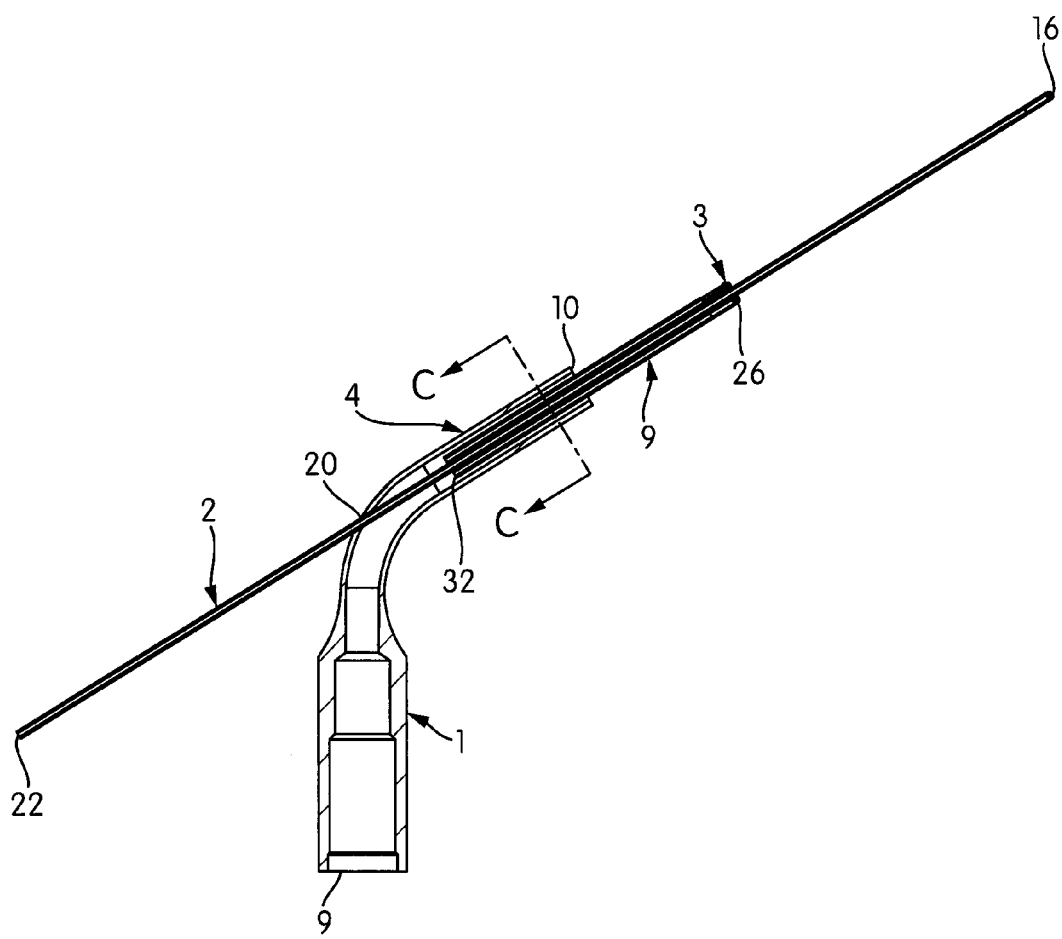
FIG. 2A is a cross section along line B-B from FIG. 1B, along with some dimensions in accordance with embodiments of the present invention.
Figure 2B:
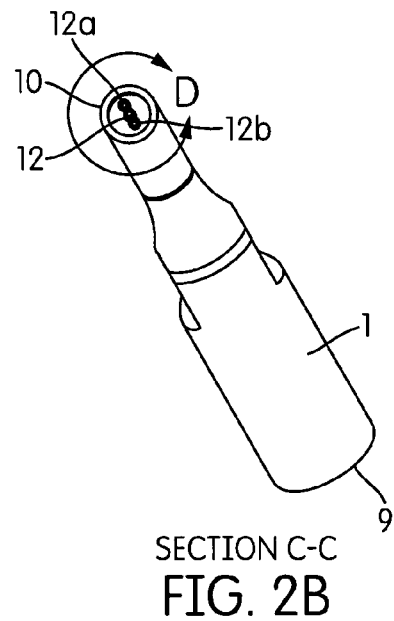
FIG. 2B is a cross section along line C-C from FIG. 2A going back into the housing of the ultrasonic tip assembly.

As shown in FIG. 2A, the outer needles 3 (e.g., irrigation needle) being of equal lengths or of varying lengths relative to each other, so that they reach different depths inside the coronal opening.

Figure 3:
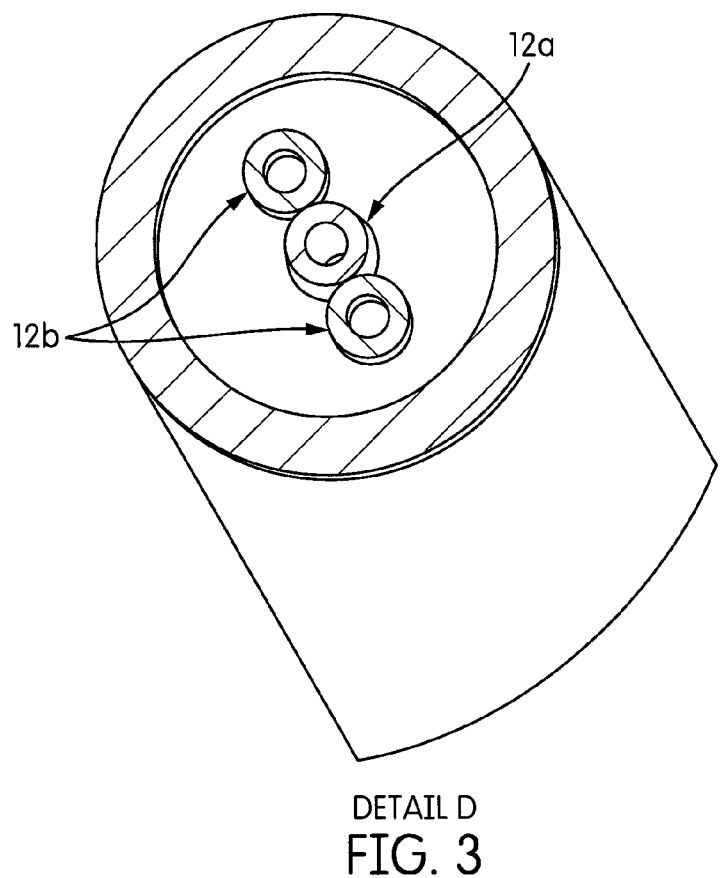
FIG. 3 is a view looking at the distal end of the ultrasonic tip assembly in accordance with embodiments of the present invention. It shows the inner aspiration needle surrounded by plurality of outer irrigation needles.
Figure 4:
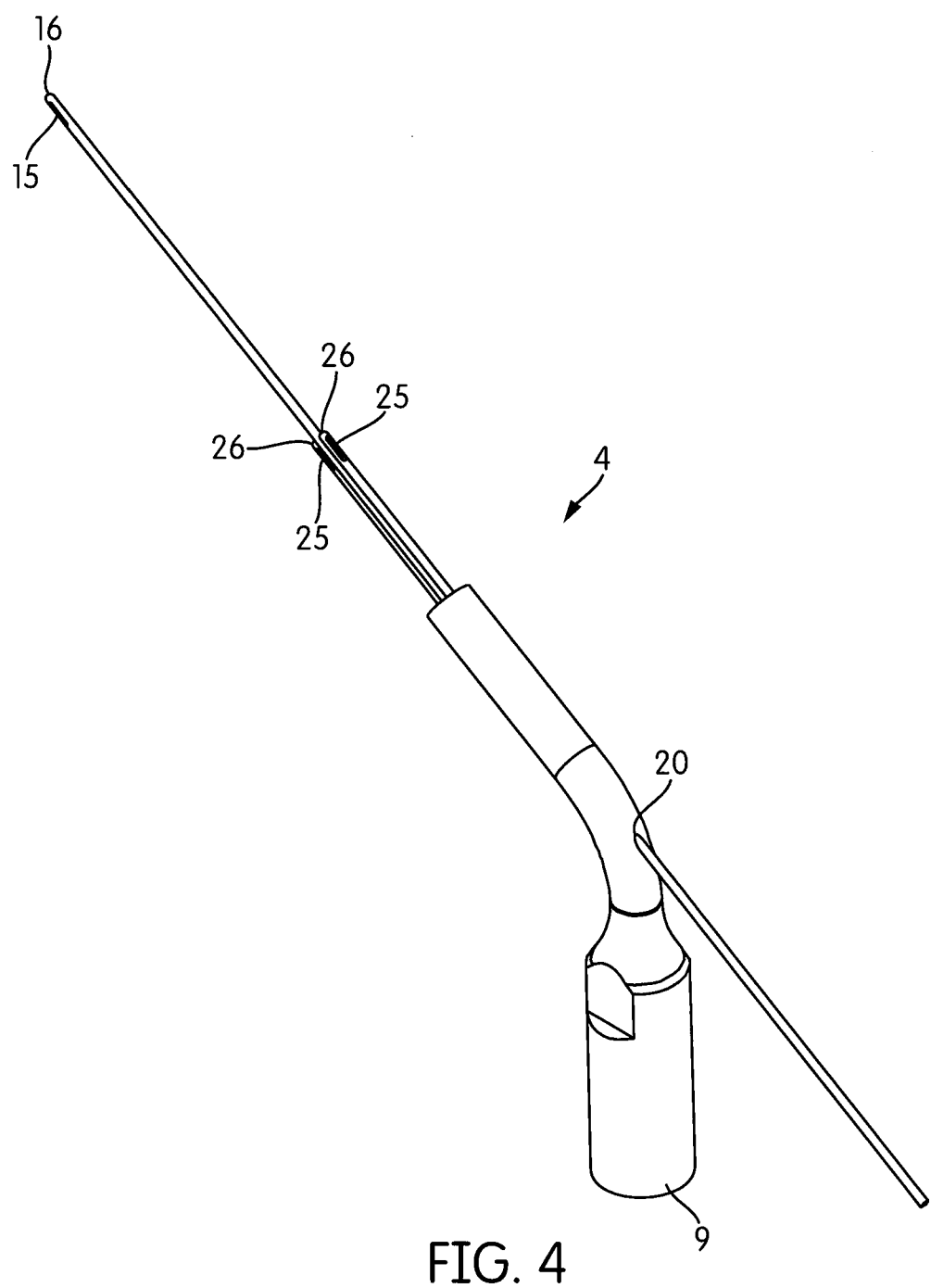
FIG. 4 is another perspective view of the ultrasonic tip assembly in accordance with embodiments of the present invention showing where the aspiration needle is brazed to the housing.

Referring to FIG. 3, the inner needle 2 (e.g., aspiration needle) is centered and surrounded by first and second outer needles 3 (e.g., irrigation needles). The outer needles 3 being spaced circumferentially equidistant from each other with the needle 2 therebetween to define a generally linear orientation.

In an alternative embodiment of the present invention, there is provided an abrading needle 2a. Abrading needle 2a is similar in material and construction to aspirating needle 2, except for the following elements. Like aspirating needle 2, abrading needle 2a is similarly used as an ultrasonically driven element.

Figure 13:
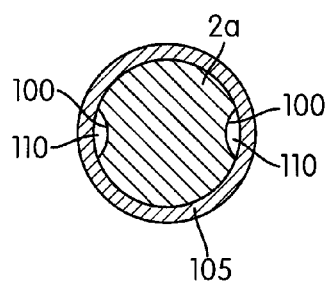
FIG. 13 is a close up sectional view taken along lines 13-13 of FIG. 12.

Abrading needle 2a is preferably of solid construction with a tip 16a they may be tapered at tip 16a as shown in the drawings or which has some other shape as may be desired. An external and preferably longitudinal groove 100 is provided in the surface of abrading needle 2a. There may be one, two grooves 100 external to abrading needle 2a for exemplary purposes. The invention is also depicted in FIG. 13 as having two regularly spaced and oppositely positioned grooves 100, although multiple grooves 100 need not be regularly spaced and need not be parallel to each other or even to the central axis of abrading needle 2a (not shown). The description herein will be directed toward the embodiment depicted in the drawings with two, regularly spaced and oppositely positioned grooves 100, it being understood that the invention is directed toward those other possible configurations.

Figure 12:
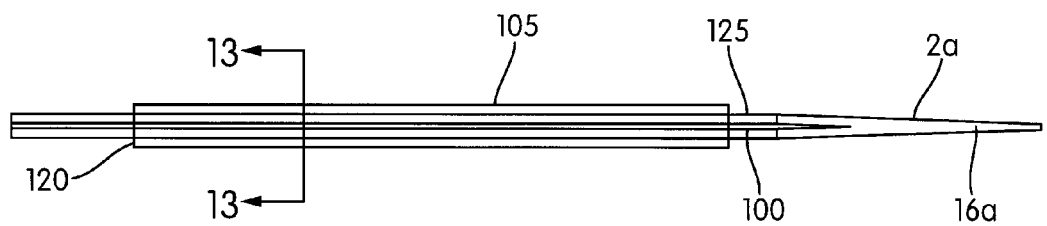
FIG. 12 is a side elevational view of the inventive component of FIG. 11.

Grooves 100 are intended to direct a flow of liquid such as water, medicaments, a disinfectant, irrigating solution or the like in the general direction of tip 16a of abrading needle 2a. It will be understood that such liquid is useful in the debridement of the root canal as was discussed hereinabove. In a further preferred embodiment, abrading needle 2a is provided with an external sleeve 105. As shown in FIGS. 12 and 13, sleeve 105 generally surrounds grooves 100, such that a fluid passageway 110 is created there between. Sleeve 105 may be metal, plastic, rubber or other suitable material. One preferred material is a medical grade shrink tubing such as those made of polyester, fluoroelastomer or the like. Liquid under pressure is forced into the space 110 (FIG. 13) created between sleeve 105 and grooves 100 at an inlet end 120 distal to tip 16a or at some other location. The liquid is thereby caused to travel or be fluidly transferred through space 110 and is discharged at some outlet 125 located more proximal to tip 16a. The length of sleeve 105 in relation to grooves 100 is not necessarily a limitation of the invention and may change depending upon the intended use of abrading needle 2a. Therefore, the locations of inlet 120 and outlet 125 may also vary depending upon use. Similarly, the wall thickness of sleeve 105 will also vary depending upon the material of construction and the intended use.

Figure 14:
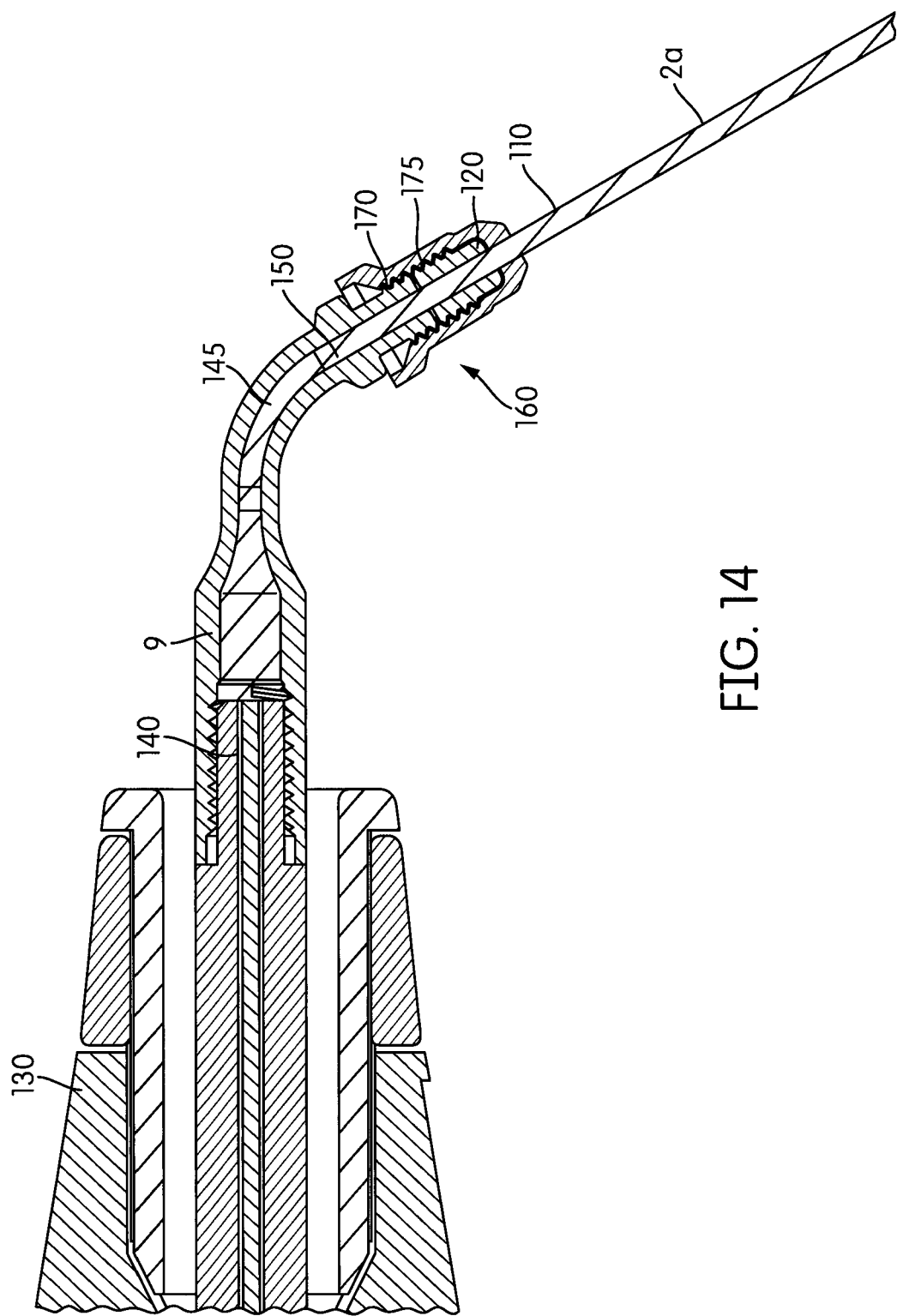
FIG. 14 is a close up, sectional side elevational view of a further embodiment of the present invention as depicted in FIG. 10.

One preferred embodiment of abrading needle 2a is shown on FIG. 14. Conduit 9 is affixed to a wand 130 having an internal fluid passageway 140 fluidly connected to a pressurized source of liquid (not shown) as is known in the industry. Conduit 9 also has an internal fluid passageway 145 fluidly connected to fluid passageway 140 of wand 130. Fluid passageway 145 traverses conduit 9 and receives therein an end 150 of abrading needle 2a in any secure manner such as by a friction fit, the use of collet and nut assembly 160 or any suitable manner. It will be appreciated that in this arrangement, grooves 100 are in fluid communication with fluid passageway 145 of conduit 9 and thereby, liquid under pressure will be caused to enter grooves 100 to be fluidly transferred in the manner above described.

Although not necessarily a required part of the invention, a collet and nut assembly 160 may include a threaded portion 170 on conduit 9 that received a nut 175 in a threaded engagement. A collet 180 may be provided such that as nut 175 is threaded onto conduit 9, collet 180 is caused to physically engage and squeeze against abrading needle 2a. It will be appreciated that in this manner, sleeve 100 is caused to be positioned between collet 180 and abrading needle 2a, forming a liquid tight connection external to abrading needle 2a. Any other suitable connection between abrading needle 2a and conduit 9 or wand 130 is within the scope of the invention.

Referring to FIGS. 6A-6C, the hypodermic aspiration needle 2 may be made from 304 stainless steel and is straight needle (e.g., hollow tubing) with a side vented hole. The needle has a passageway 6 extending at least partially through the needle, substantial length of the needle or at least from one end to the other end. The pathway 6 provides a single continuous, uninterrupted flow path for receiving the aspirated irrigants and debris resulting from the cleaning of root canal.

In the embodiment shown, the aspiration needle 2 may be made from 28 gauge 304 stainless steel, although other gauge needles and materials can be used where it is determined to result in desired performance. The length of the aspiration needle 2 may be greater than 5 mm, preferably greater than 15 mm, and most preferably greater than 25 mm. If a plurality of aspiration needles may be present, the aspiration needles can either all be the same length or of varying lengths relative to each other. As shown in FIG. 6 the side vented hole 15 is 1 mm long and 0.2 mm wide, although different hole sizes and configurations can be used; as well as the hole being at the tip instead of side vented.

Figure 7A:
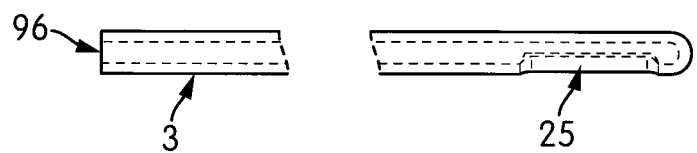
FIGS. 7A-7C illustrates various views of the outer irrigation needles of the tip assembly.
Figure 7B:
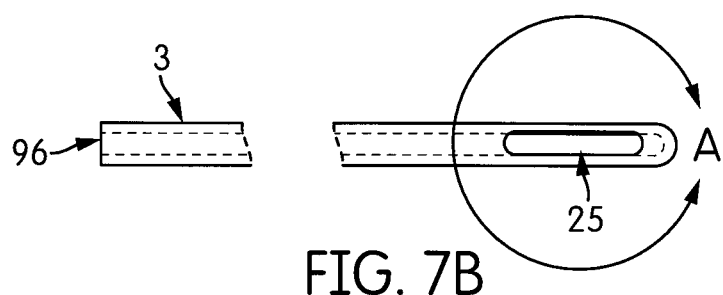
Figure 7C:
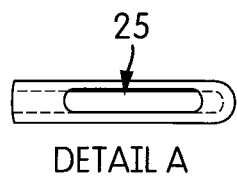

Referring to FIGS. 7A-7C, the hypodermic irrigation needles 3 are preferably made from 304 stainless steel and is straight needle (e.g., hollow tubing) with a side vented hole 25. The irrigation needles have a passageway 96 extending at least partially through the needle, a substantial length of the needle or at least from one end to the other end of the irrigation needle. The pathway 96 provides a single continuous, uninterrupted flow path for irrigants to flow into the coronal aspect of the tooth.

In the embodiment shown, the irrigation needle may be made from 28 gauge 304 stainless steel, although other gauge needles and materials can be used as well. The length of the irrigation needle may be greater than 2 mm, preferably greater than 6 mm, most preferably greater than 10 mm. If a plurality of irrigation needles may be present, the irrigation needles can either all be the same length or of varying lengths relative to each other. As shown in FIG. 7 the side vented hole 5 is 1 mm long and 0.2 mm wide, although different hole sizes and configurations can be used, as well as the hole being at the tip.

Figure 5A:
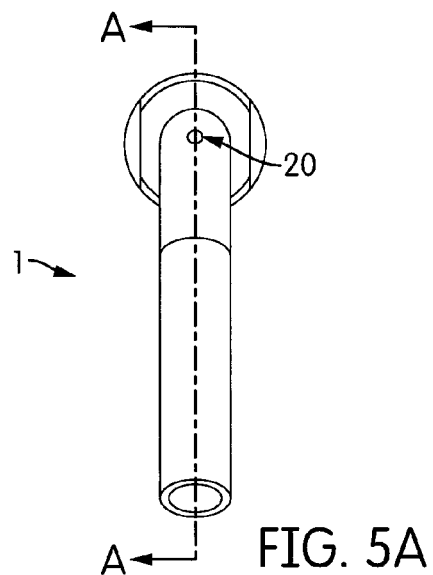
FIGS. 5A-5C illustrates various views of the housing of the tip assembly.
Figure 5B:
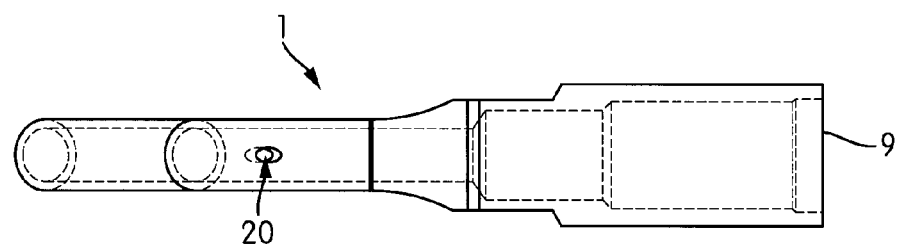
Figure 5C:
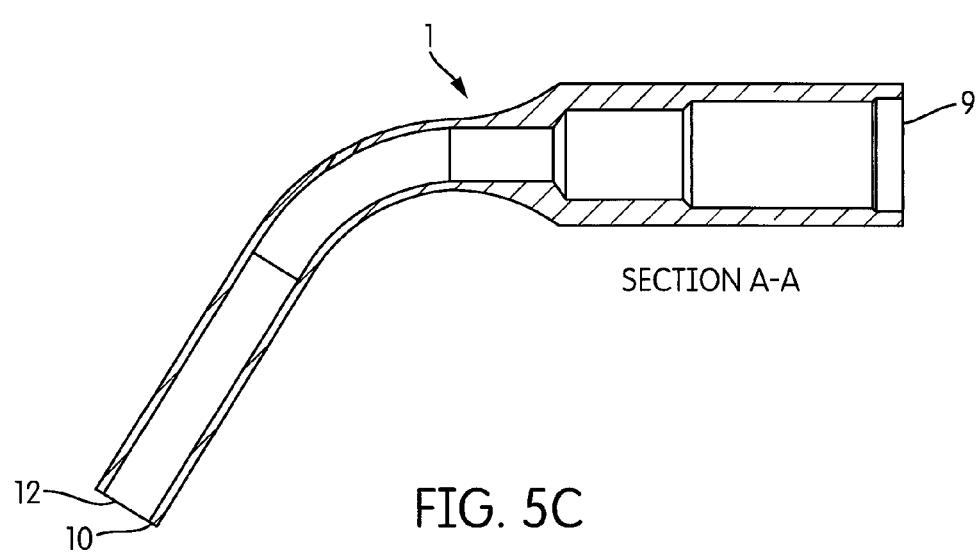

With reference to one specific example of FIG. 5, the housing 1 is shown with preferred dimensions for this embodiment. The housing 1 may be made of 17-4 stainless steel. There is a 2 mm hole 20 through one wall of the housing 1 for the 28 gauge inner aspiration needle 2 to extend through. The inner aspiration needle 2 and outer irrigation needles 3 may be brazed, welded, adhered, or otherwise liquid tight between the housing to prevent any leakage.

Figure 8:
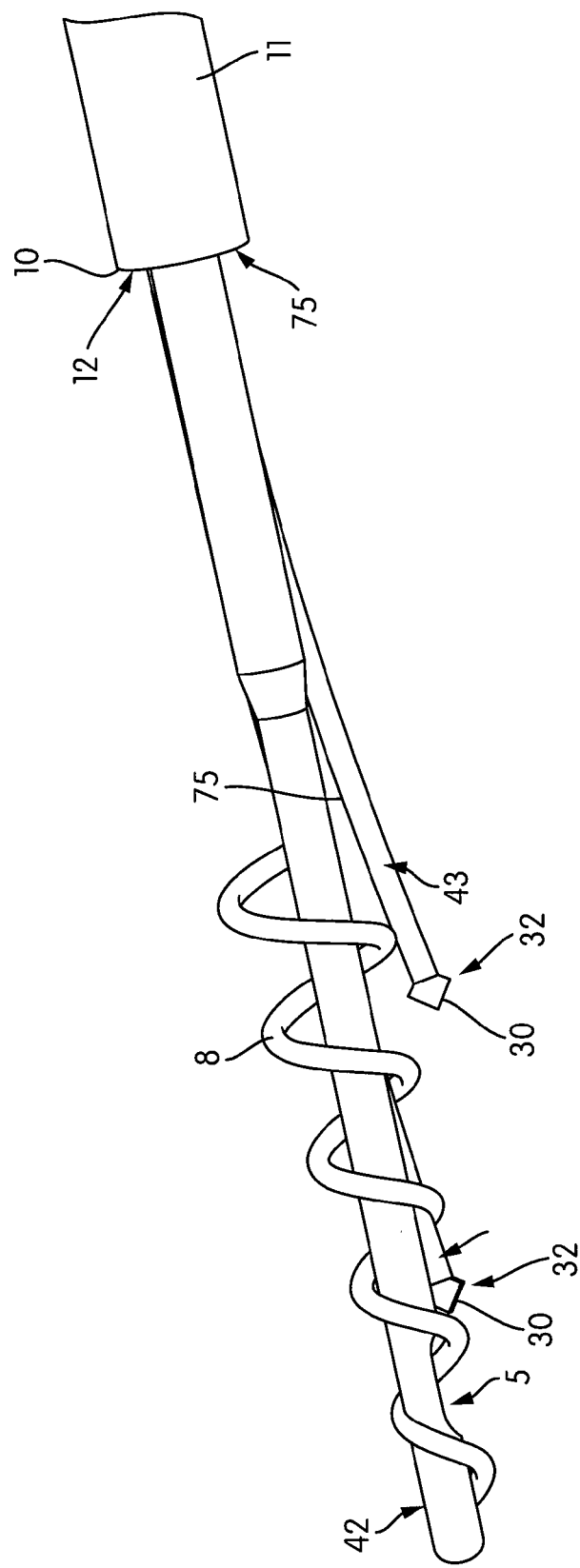
FIG. 8 illustrates a side view of an alternative embodiment of the present invention.

FIG. 8 shows an alternative embodiment. This embodiment incorporates an inner needle 42 (e.g., aspiration needle), at least one axially wound needle/wire 8 (e., spirally wound) having a tapered diameter. It is appreciated that the needle/wire 8 may be a hollow irrigation needle or a solid wire. Also included are one more needles/wires 43 surrounding the perimeter of the inner aspiration needle 42. The torsional wound needle 8 will provide a rotational flow about the inner aspiration needle 42. The individual needles 43 are different lengths and will have nodes and anti-nodes. These nodes and anti-nodes will be at various depths in the canal creating more acoustic streaming and agitation all along the depth of the canal. The individual needles 43 may also have sharp edges 30 on their tips 32 creating more points of cavitation. When the needle/wire 8 is provided as a solid wire, irrigant may be supplied through an opening 12 (at the distal free end 10) of the housing 11 along spaces 75 between the wires 8 and the aspiration needle 42.

Figure 9:
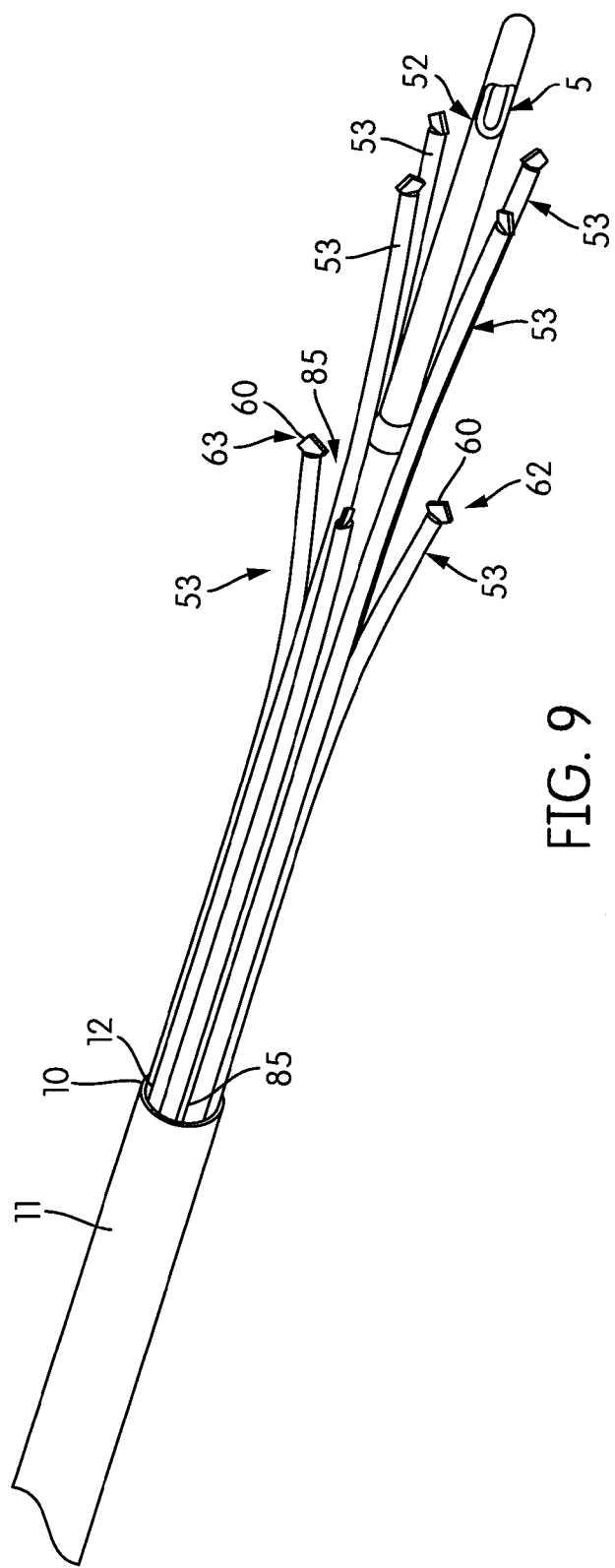
FIG. 9 illustrates a side view of an alternative embodiment of the present invention.
Figure 10:
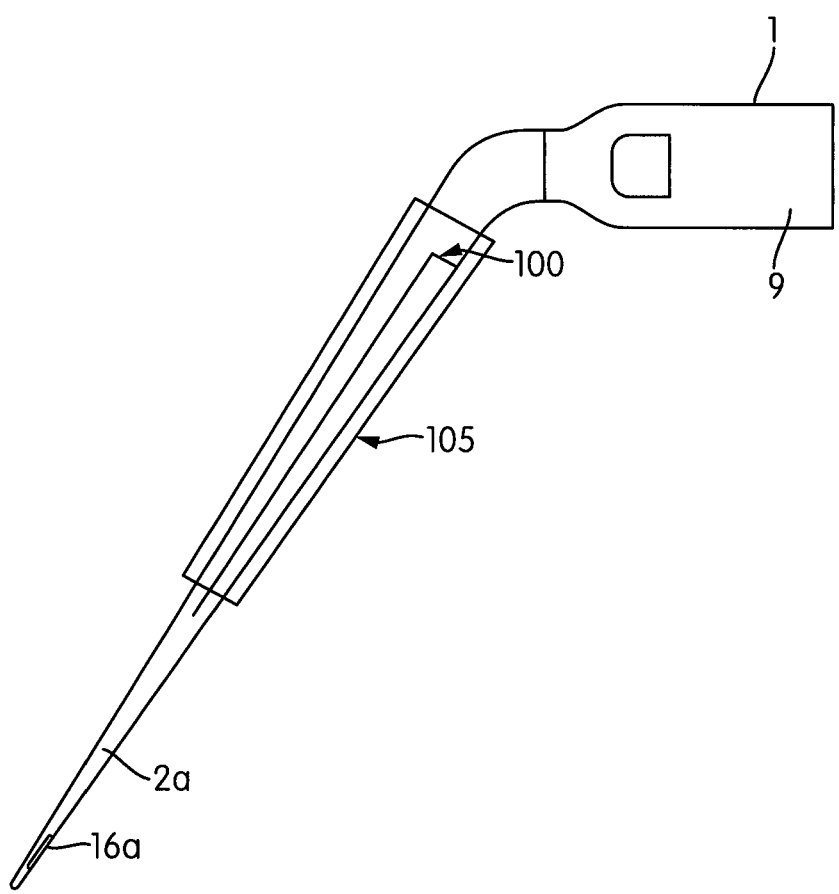
FIG. 10 is a side, elevational view of an alternative embodiment of the present invention.
Figure 11:
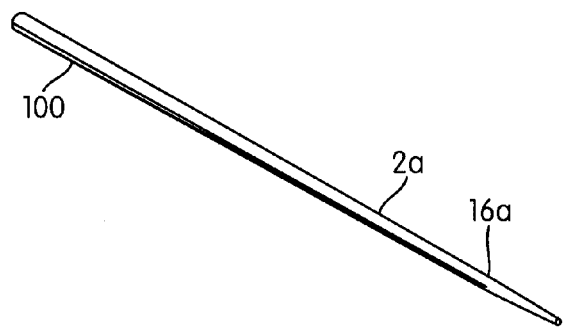
FIG. 11 is a perspective view of one component of the invention depicted in FIG. 10.

FIG. 9 also shows another alternative embodiment. This embodiment incorporates multiple needles/wires 53 (e.g., irrigation needles) around the perimeter of an inner needle 52 (e.g., aspiration needle). It is appreciated that the needle/wire 53 may be a hollow irrigation needle or a solid wire. The advantage of this design is that the individual needles 53 will more thoroughly fill and clean the coronal area. The individual needles 53 are different in lengths and will have nodes and anti-nodes. These nodes and anti-nodes will be at various depths in the canal creating more acoustic streaming and agitation all along the depth of the canal. The individual needles/wires 53 will also have sharp edges 60 on their tips 62 creating more points of cavitation. When the needle/wire 53 are provided as a solid wire, irrigant may be supplied through the opening 12 (at the distal free end 10) of the housing 11 along spaces 85 between the wires 53 and the aspiration needle 53.

The invention described herein has many other advantages. The needle has a single continuous flow path, which eliminates potential leak paths. As no joints or discontinuities are present, corrosion is limited. Inherent stress concentrations are also eliminated, thereby allowing the tip assembly to be reliable during vibration. The configuration of the tip assembly guides and transfers the ultrasonic vibration and energy in the planes of motion, which provides proper agitation to the irrigants. The tip assembly can also be disposable, thereby requiring that a new tip assembly be used for each patient and insuring that the tip assembly will be sterile prior to use.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While preferred embodiments of the present invention have been shown and described herein, it will be obvious to those skilled in the art that such embodiments are provided by way of example only. Numerous variations, changes, and substitutions will be apparent to those skilled in the art without departing from the invention. Other foreseen embodiments or uses for the present invention include the use of the invention in the field of phacoemulsification, where a tip assembly such as the present invention may offer many advantages. Accordingly, it is intended that the invention be limited only by the scope of the appended claims.

What is claimed is:

1. A tip assembly for use with a dental tool, the tip assembly comprising:
   a housing having a conduit for attaching to the dental tool;
   an inner aspiration needle having a passageway extending at least partially through needle, a substantial length of the needle, or at least from one end to the other end the passageway providing a single continuous path to aspirate the irrigant and debris from the root canal cavity of the tooth; and
   a plurality of outer wires, surrounding inner aspiration needle; and
   wherein the inner aspiration needle and outer wires are connected together at a point or along a portion therebetween to achieve a first predetermined resonant frequency of the inner aspiration needle, and
   wherein the plurality of outer wires extend spirally around the aspiration needle;
   wherein the plurality of outer wires includes a first outer wire and a second outer wire, the first outer wire extending spirally around the aspiration needle and a tip portion of the second outer wire being bent or curved away from the aspiration needle.

2. A tip assembly for use with an ultrasonic transducer comprising:
   an abrading needle operatively connected to the ultrasonic transducer;
   said abrading needle having a working tip and a connecting end;
   at least one groove on the exterior of said needle; and
   a sleeve at least partially covering said at least one groove;
   such that a fluid passageway is effectively formed between said at least one groove and said sleeve.

3. A tip assembly as in claim 2, wherein said sleeve is formed from a tube.

4. A tip assembly as in claim 3 wherein said tube is metal, plastic or rubber.

5. A tip assembly as in claim 3 wherein said tube is made from a medical grade, shrink tube material.

6. A tip assembly as in claim 2 further comprising a conduit positioned between said abrading needle and the ultrasonic transducer.

7. A tip assembly as in claim 6, wherein said conduit includes a fluid passageway fluidly connecting a source of pressurized fluid with said at least one groove.

* * * * *